US007201905B2

(12) United States Patent
Chen et al.

(10) Patent No.: US 7,201,905 B2
(45) Date of Patent: Apr. 10, 2007

(54) BI-FUNCTIONAL CANCER TREATMENT AGENTS

(75) Inventors: Wen Y. Chen, Simpsonville, SC (US); Thomas E. Wagner, Greer, SC (US)

(73) Assignee: Greenville Hospital System, Greenville, SC (US)

( * ) Notice: Subject to any disclaimer, the term of this patent is extended or adjusted under 35 U.S.C. 154(b) by 905 days.

(21) Appl. No.: 09/815,306

(22) Filed: Mar. 23, 2001

(65) Prior Publication Data

US 2002/0068043 A1    Jun. 6, 2002

(51) Int. Cl.
 *A61K 39/00* (2006.01)
(52) U.S. Cl. .............................. 424/192.1; 424/185.1; 424/195.11
(58) Field of Classification Search ............... 435/47; 424/192.1, 185.1, 195.11
See application file for complete search history.

(56) References Cited

U.S. PATENT DOCUMENTS 5,314,995 A * 5/1994 Fell et al. ................... 530/351
6,429,186 B1 * 8/2002 Fuh et al. ....................... 514/2

FOREIGN PATENT DOCUMENTS

WO   WO 98/08949   *   3/1998
WO   WO 99/58142 A1   11/1999

OTHER PUBLICATIONS

Macieira-Coelho A Biogerontology 2001;2(3):179-92.*
Mocellin S et al. J. Immunother Sep.-Oct. 2001; 25(5):392-407.*
Lode et al. Proc Natl Acad Sci USA Feb. 1999; 96(4):1591-1596.*
Gillies et al. J. Immuno 1998; 160(12):6195-203.*
Bulfone-Paus S et al. Transplantation 2000 Spr 15;69(7):1386-91.*
Sissom et al (Am J. Pathol. 1988;133(3):589-95).*
Gillies et al (J. Immunology, 1998;160(12):6195-6203).*
Gura (Science, v278, 1997, pp. 1041-1042).*
Kelly et al (Mol. Cell. Endocrinology 2002;197:127-131).*
Rozengurt (Curr. Opin. Oncology 1999;11(2):116).*
Jones et al (Leuk Lymphoma. Jun. 2002;43(6):1313-21).*
Biology of Female Cancers, CRC Press LLC, pp. 31-42, 1997.
Cleveenger et al., "Expression of Prolactin and Prolactin Receptor in Human Breast Carcinoma", American Journal of Pathology, American Society for Investigative Pathology, vol. 146, No. 3, pp. 695-705, Mar. 1995.

Ginsburg et al., "Prolactin Synthesis and Secretion by Human Breast Cancer Cells"; Cancer Research, An Official Journal of the American Association for Cancer Research, vol. 55, No. 12, pp. 2591-2595, Jun. 15, 1995.
Wnnbo et al., "Transgenic Mice Overexpressing the Prolactin Gene Develop Dramatic Enlargement of the Prostate Gland", Endocrinology, The Endocrine Society, vol. 38, No. 10, pp. 4410-4415, Oct. 1997.
Aragona et al, "Specific Prolactin Binding Sites in the Prostate and Testis of Rats", Endocrinology, The Endocrine Society, vol. 97, No. 3, pp. 677-684, Sep. 1975.
Leake et al., "Characterization of the Prolactin Receptor in Human Prostate"; The Journal of Endocrinology, The Journal of Endocrinology Limited, vol. 99, No. 2, pp. 321-328, Nov. 1983.
Hammond et al., "Serum FSH, LH and Prolactin in Normal Males and Patients with Prostatic Diseases", Clinical Endocrinology, Blackwell Scientific Publications, vol. 7, No. 2, pp. 129-135, Aug. 1977.
"Influence of Age on Serum Prolactin Levels in Women and Men", British Medical Journal, vol. 4, No. 5999, pp. 738-739, Dec. 27, 1975.
Boon., "Toward a Genetic Analysis of Tumor Rejection Antigens", Advances in Cancer Research, Academic Press, Inc., vol. 58, pp. 177-210, 1992.
Urban et al., "Tumor Antigens", Annual Review of Immunology, Annual Reviews Inc., vol. 10, pp. 617-644, 1992.
"Selective in Vitro Growth of T Lymphocytes from Normal Human Bone Marrows", Science, American Association for the Advancement of Science, vol. 193, No. 4257, pp. 1007-1008, Sep. 10, 1976.
Hendrzak et al., "Interferons and Other Cytokines", Cancer Therapeutics, Human Press, pp. 263-282, 1997.
Rosenberg et al., "Use of Tumor Infiltrating Lymphocytes and Interleukin-2 in the Immunotherapy of Patients with Metastaic Melanoma", The New England Journal of Medicine, The Massachusetts Medical Society, vol. 319, No. 25, pp. 1676-1680, Dec. 22, 1988.
Maas et al., "Transfer of Tumor Immunity by Both $CD4^+$ and $DC8^+$ Tumor Infiltrating T Lymphocytes Activated *in vivo* by IL-2 Therapy of Tumor Bearing Mice", Immunobiology, vol. 188, Mo. 3, pp. 281-292, 1993.

(Continued)

*Primary Examiner*—Christopher H. Yaen
(74) *Attorney, Agent, or Firm*—Foley & Lardner LLP

(57) ABSTRACT

A novel fusion protein, comprising a receptor-antagonizing domain and a positive immunomodulator domain, characterized, for example, by its ability to block apoptosis and/or inhibit endocrine response, is useful in treating cancer. For example, a human prolactin antagonist-interleukin 2 (hPRLA-IL-2) fusion protein combines apoptosis induction and immuno-therapy to combat cancer in the breast or prostate.

22 Claims, 5 Drawing Sheets

OTHER PUBLICATIONS

Forni et al., "Interleukin 2 Activated Tumor Inhibition in Vivo Depends on the Systemic Involvement of Host Immunoreactivity", Journal of Immunology, The American Society of Immunologists, vol. 138, No. 11, pp. 4033-4041, Jun. 1, 1987.

Fearon et al., "Interleukin-2 Production by Tumor Cells Bypasses T Helper Function in the Generation of an Antitumor Response", Cell, Cell Press, vol. 60, No. 3, pp. 397-403, Feb. 9, 1990.

Pardoll, "Cancer Vaccines", Immunology Today, Elsevier Science Publishers Ltd., vol. 14, No. 6, pp. 310-316, 1993.

Reisfeld et al., "Recombinant Antibody Fusion Proteins for Cancer Immunotherapy", Attempts to Understand Metastasis Formation III, Springer, pp. 28-53, 1996.

Gillies et al., "Antibody-Targeted Interleukin 2 Stimulates T-Cell Killing of Autologous Tumor Cells", Immunology, Proceedings of the National Academy of Sciences, of the United States of America, vol. 89, No. 4, pp. 1428-1432, Feb. 1992.

Sabzevari et al., " A Recombinant Antibody-Interleukin 2 Fusion Protein Suppresses Growth of Hepatic Human Neuroblastoma Metastases in Severe Combined Immunodeficiency Mice", Immunology, Proceedings of the National Academy of Sciences, of the United States of America, vol. 91, No. 20, pp. 9626-9630, Sep. 1994.

Chen et al., "A Human Prolactin Antagonist, hPRL-G129R, Inhibits Breast Cancer Cell Proliferation through Induction of Apoptosis", Clinical Cancer Research, vol. 5, No. 11, pp. 3583-3593, Nov. 1999.

Herbert et al., "Chelerythrine is a Potent and Specific Inhibitor of Protein Kinase C", Biochemical and Biophysical Research Communications, Academic Press, Inc., vol. 172, No. 3, pp. 993-999, Nov. 15, 1990.

Paris et al., "Bacterial Production and Purification of Recombinant Human Prolactin", Biotechnology and Applied Biochemistry, Academic Press, Inc., vol. 12, No. 4, pp. 436-449, 1990.

Gluzman, "SV40-Transformed Simian Cells Support the Replication of Early SV40 Mutants", Cell, MIT, vol. 23, No. 1, pp. 175-182, Jan. 1981.

Logan et al., "Adenovirus Tripartite Leader Sequence Enhances Translation of mRNAs Late After Infection", Biochemistry, Proceedings of the National Academy of Sciences of the United States of America, vol. 81, No. 12, pp. 3655-3659, Jun. 1984.

Chen et al., "Expression of a Mutated Bovine Growth Hormone Gene Suppresses Growth of Transgenic Mice", Cell Biology, Proceedings of the National Academy of Sciences of the United States of America, vol. 87, No. 13, pp. 5061-5065, Jul. 1990.

Reynolds et al., "Expression of Prolactin and Its Receptor in Human Breast Carcinoma", Endocrinology, The Endocrine Society, vol. 138, No. 12, pp. 5555-5560, Dec. 1997.

Sirbsku et al., "Estrogen Mitogenic Action, IL Negative Regulation of the Steroid Hormone-Responsive Growth of Cell Lines Derived from Human and Rodent Target Tissue Tumors and Conceptual Implications", Journal of the Society for In Vitro Biology, Invitro, vol. 36, No. 7, pp. 428-446, Jul.-Aug. 2000.

Sirbasku, "Estrogen Induction of Growth Factors Specific for Hormone-Responsive Mammary, Pituitary, and Kidney Tumor Cells", Cell Biology, Proceedings of the National Academy of Sciences of the United States of America, vol. 75, No. 8, pp. 3786-3790, Aug. 1978.

Chen et al., "Amino Acid Residues in the Third α-Helix of Growth Hormone Involved in Growth Promoting Activity", Molecular Endocrinology, the Endocrine Society, vol. 9, No. 3, pp. 292-302, 1995.

Dickson et al., "Hormonal Control of Human Breast Cancer Cell Lines", Cancer Surveys, Imperial Cancer Research Fund, vol. 5, No. 3, pp. 617-624, 1986.

Bole-Feysot, et al.; Prolactin (PRL) and Its Receptor: Actions, Signal Transduction Pathways and Phenotypes Observed in PRL Receptor Knockout Mice; Endocrine Reviews 19(3): 225-268; 1998 by The Endocrine Society.

Harvey, Stephen et al., "Growth Hormone," CRC Press, 1995, pp. 7-8.

R.A. Reisfeld et al., "Recombinant Antibody Fusion Proteins for Cancer Immunotherapy," *Current Topics in Microbiology and Immunology* (1996), 213(3):27-53, XP001030927.

* cited by examiner

SEQUENCE LISTING

```
<160> NUMBER OF SEQ ID NOS: 33

<210> SEQ ID NO 1
<211> LENGTH: 227
<212> TYPE: PRT
<213> ORGANISM: Homo sapiens

<400> SEQUENCE: 1

Met Asn Ile Lys Gly Ser Pro Trp Lys Gly Ser Leu Leu Leu Leu Leu
  1               5                  10                  15

Val Ser Asn Leu Leu Leu Cys Gln Ser Val Ala Pro Leu Pro Ile Cys
             20                  25                  30

Pro Gly Gly Ala Ala Arg Cys Gln Val Thr Leu Arg Asp Leu Phe Asp
         35                  40                  45

Arg Ala Val Val Leu Ser His Tyr Ile His Asn Leu Ser Ser Glu Met
     50                  55                  60

Phe Ser Glu Phe Asp Lys Arg Tyr Thr His Gly Arg Gly Phe Ile Thr
 65                  70                  75                  80

Lys Ala Ile Asn Ser Cys His Thr Ser Ser Leu Ala Thr Pro Glu Asp
                 85                  90                  95

Lys Glu Gln Ala Gln Gln Met Asn Gln Lys Asp Phe Leu Ser Leu Ile
            100                 105                 110

Val Ser Ile Leu Arg Ser Trp Asn Glu Pro Leu Tyr His Leu Val Thr
        115                 120                 125

Glu Val Arg Gly Met Gln Glu Ala Pro Glu Ala Ile Leu Ser Lys Ala
    130                 135                 140

Val Glu Ile Glu Glu Gln Thr Lys Arg Leu Leu Glu Gly Met Glu Leu
145                 150                 155                 160

Ile Val Ser Gln Val His Pro Glu Thr Lys Glu Asn Glu Ile Tyr Pro
                165                 170                 175

Val Trp Ser Gly Leu Pro Ser Leu Gln Met Ala Asp Glu Glu Ser Arg
            180                 185                 190

Leu Ser Ala Tyr Tyr Asn Leu Leu His Cys Leu Arg Arg Asp Ser His
        195                 200                 205

Lys Ile Asp Asn Tyr Leu Lys Leu Leu Lys Cys Arg Ile Ile His Asn
    210                 215                 220
```

```
Asn Asn Cys
225

<210> SEQ ID NO 2
<211> LENGTH: 21
<212> TYPE: PRT
<213> ORGANISM: Homo sapiens

<400> SEQUENCE: 2

Ile Glu Glu Gln Thr Lys Arg Leu Leu Arg Gly Met Glu Leu Ile Val
 1               5                  10                  15

Ser Gln Val His Pro
            20

<210> SEQ ID NO 3
<211> LENGTH: 21
<212> TYPE: PRT
<213> ORGANISM: Rattus sp.

<400> SEQUENCE: 3

Ile Glu Glu Gln Asn Lys Arg Leu Leu Glu Gly Ile Glu Lys Ile Ile
 1               5                  10                  15

Gly Gln Ala Tyr Pro
            20

<210> SEQ ID NO 4
<211> LENGTH: 21
<212> TYPE: PRT
<213> ORGANISM: Mus sp.

<400> SEQUENCE: 4

Ile Glu Glu Gln Asn Lys Gln Leu Leu Glu Gly Val Glu Lys Ile Ile
 1               5                  10                  15

Ser Gln Ala Tyr Pro
            20

<210> SEQ ID NO 5
<211> LENGTH: 21
<212> TYPE: PRT
<213> ORGANISM: Cricetus sp.

<400> SEQUENCE: 5

Ile Gly Glu Gln Asn Lys Arg Leu Leu Glu Gly Ile Glu Lys Ile Leu
 1               5                  10                  15

Gly Gln Ala Tyr Pro
            20

<210> SEQ ID NO 6
<211> LENGTH: 21
<212> TYPE: PRT
<213> ORGANISM: Cetacea sp.

<400> SEQUENCE: 6

Glu Glu Glu Glu Asn Lys Arg Leu Leu Glu Gly Met Glu Lys Ile Val
 1               5                  10                  15

Gly Gln Val His Pro
            20

<210> SEQ ID NO 7
<211> LENGTH: 21
<212> TYPE: PRT
<213> ORGANISM: Mustela sp.
```

-continued

```
<400> SEQUENCE: 7

Ile Glu Glu Glu Asn Arg Arg Leu Leu Glu Gly Met Glu Lys Ile Val
 1               5                  10                  15

Gly Gln Val His Pro
            20

<210> SEQ ID NO 8
<211> LENGTH: 21
<212> TYPE: PRT
<213> ORGANISM: Bos sp.

<400> SEQUENCE: 8

Ile Glu Glu Gln Asn Lys Arg Leu Ile Glu Gly Met Glu Met Ile Phe
 1               5                  10                  15

Gly Gln Val Ile Pro
            20

<210> SEQ ID NO 9
<211> LENGTH: 21
<212> TYPE: PRT
<213> ORGANISM: Ovis sp.

<400> SEQUENCE: 9

Glu Glu Glu Glu Asn Lys Arg Leu Leu Glu Gly Met Glu Asn Ile Phe
 1               5                  10                  15

Gly Gln Val Ile Pro
            20

<210> SEQ ID NO 10
<211> LENGTH: 21
<212> TYPE: PRT
<213> ORGANISM: Porcine sp.

<400> SEQUENCE: 10

Ile Glu Glu Gln Asn Lys Arg Leu Leu Glu Gly Met Glu Lys Ile Val
 1               5                  10                  15

Gly Gln Val His Pro
            20

<210> SEQ ID NO 11
<211> LENGTH: 21
<212> TYPE: PRT
<213> ORGANISM: Camelus sp.

<400> SEQUENCE: 11

Ile Glu Glu Gln Asn Lys Arg Leu Leu Glu Gly Met Glu Lys Ile Val
 1               5                  10                  15

Gly Gln Val His Pro
            20

<210> SEQ ID NO 12
<211> LENGTH: 21
<212> TYPE: PRT
<213> ORGANISM: Equus caballus

<400> SEQUENCE: 12

Glu Ile Glu Gln Asn Arg Arg Leu Leu Glu Gly Met Glu Lys Ile Val
 1               5                  10                  15

Gly Gln Val Gln Pro
            20
```

```
<210> SEQ ID NO 13
<211> LENGTH: 21
<212> TYPE: PRT
<213> ORGANISM: Elephantus sp.

<400> SEQUENCE: 13

Val Lys Glu Glu Asn Gln Arg Leu Leu Glu Gly Ile Glu Lys Ile Val
 1               5                  10                  15

Asp Gln Val His Pro
            20

<210> SEQ ID NO 14
<211> LENGTH: 21
<212> TYPE: PRT
<213> ORGANISM: Unknown Organism
<220> FEATURE:
<223> OTHER INFORMATION: Description of Unknown Organism: Ancestral
      mammal

<400> SEQUENCE: 14

Ile Glu Glu Glu Asn Lys Arg Leu Leu Glu Gly Met Glu Lys Ile Val
 1               5                  10                  15

Gly Gln Val His Pro
            20

<210> SEQ ID NO 15
<211> LENGTH: 21
<212> TYPE: PRT
<213> ORGANISM: Gallus sp.

<400> SEQUENCE: 15

Ile Glu Glu Gln Asn Lys Arg Leu Leu Glu Gly Met Glu Lys Ile Val
 1               5                  10                  15

Gly Arg Val His Ser
            20

<210> SEQ ID NO 16
<211> LENGTH: 21
<212> TYPE: PRT
<213> ORGANISM: Meleagris gallopavo

<400> SEQUENCE: 16

Ile Glu Glu Gln Asp Lys Arg Leu Leu Glu Gly Met Glu Lys Ile Val
 1               5                  10                  15

Gly Arg Ile His Ser
            20

<210> SEQ ID NO 17
<211> LENGTH: 21
<212> TYPE: PRT
<213> ORGANISM: Turtur sp.

<400> SEQUENCE: 17

Ile Glu Glu Gln Asn Lys Arg Leu Leu Glu Gly Met Glu Lys Ile Val
 1               5                  10                  15

Gly Gln Val His Pro
            20

<210> SEQ ID NO 18
<211> LENGTH: 21
<212> TYPE: PRT
<213> ORGANISM: Crocodilus sp.

<400> SEQUENCE: 18
```

```
Ile Glu Glu Gln Asn Lys Arg Leu Leu Glu Gly Met Glu Lys Ile Ile
 1               5                  10                  15

Gly Arg Val Gln Pro
            20

<210> SEQ ID NO 19
<211> LENGTH: 21
<212> TYPE: PRT
<213> ORGANISM: Lacerta sp.

<400> SEQUENCE: 19

Ile Glu Glu Gln Asn Lys Arg Leu Leu Glu Gly Met Glu Lys Val Ile
 1               5                  10                  15

Gly Arg Val Gln Pro
            20

<210> SEQ ID NO 20
<211> LENGTH: 21
<212> TYPE: PRT
<213> ORGANISM: Unknown Organism
<220> FEATURE:
<223> OTHER INFORMATION: Description of Unknown Organism: Ancestral
      amniote

<400> SEQUENCE: 20

Ile Glu Glu Gln Asn Lys Arg Leu Leu Glu Gly Met Glu Lys Ile Val
 1               5                  10                  15

Gly Gln Val His Pro
            20

<210> SEQ ID NO 21
<211> LENGTH: 21
<212> TYPE: PRT
<213> ORGANISM: Xenopus sp.

<400> SEQUENCE: 21

Val Glu Glu Gln Asn Lys Arg Leu Leu Glu Gly Met Glu Lys Ile Val
 1               5                  10                  15

Gly Arg Ile His Pro
            20

<210> SEQ ID NO 22
<211> LENGTH: 21
<212> TYPE: PRT
<213> ORGANISM: Rana catesbeiana

<400> SEQUENCE: 22

Val Glu Glu Gln Thr Lys Arg Leu Leu Glu Gly Met Glu Arg Ile Ile
 1               5                  10                  15

Gly Arg Ile Gln Pro
            20

<210> SEQ ID NO 23
<211> LENGTH: 21
<212> TYPE: PRT
<213> ORGANISM: Dipnoi sp.

<400> SEQUENCE: 23

Val Glu Asp Gln Thr Lys Gln Leu Ile Glu Gly Met Glu Lys Ile Leu
 1               5                  10                  15

Ser Arg Met His Pro
            20
```

```
<210> SEQ ID NO 24
<211> LENGTH: 21
<212> TYPE: PRT
<213> ORGANISM: Unknown Organism
<220> FEATURE:
<223> OTHER INFORMATION: Description of Unknown Organism: Tilapia

<400> SEQUENCE: 24

Met Gln Gln Tyr Ser Lys Ser Leu Lys Asp Gly Leu Asp Val Leu Ser
 1               5                  10                  15

Ser Lys Met Gly Ser
            20

<210> SEQ ID NO 25
<211> LENGTH: 21
<212> TYPE: PRT
<213> ORGANISM: Unknown Organism
<220> FEATURE:
<223> OTHER INFORMATION: Description of Unknown Organism: Tilapia

<400> SEQUENCE: 25

Met Gln Glu His Ser Lys Asp Leu Lys Asp Gly Leu Asp Ile Leu Ser
 1               5                  10                  15

Ser Lys Met Gly Pro
            20

<210> SEQ ID NO 26
<211> LENGTH: 21
<212> TYPE: PRT
<213> ORGANISM: Cyprinus carpio

<400> SEQUENCE: 26

Leu Gln Glu Asn Ile Asn Ser Leu Gly Ala Gly Leu Glu His Val Phe
 1               5                  10                  15

Asn Lys Met Asp Ser
            20

<210> SEQ ID NO 27
<211> LENGTH: 21
<212> TYPE: PRT
<213> ORGANISM: Cyprinus carpio

<400> SEQUENCE: 27

Leu Gln Asp Asn Ile Asn Ser Leu Gly Ala Gly Leu Glu Arg Val Val
 1               5                  10                  15

His Lys Met Gly Ser
            20

<210> SEQ ID NO 28
<211> LENGTH: 21
<212> TYPE: PRT
<213> ORGANISM: Cyprinus carpio

<400> SEQUENCE: 28

Leu Gln Asp Asn Ile Asn Ser Leu Val Pro Gly Leu Glu His Val Val
 1               5                  10                  15
```

```
His Lys Met Gly Ser
            20

<210> SEQ ID NO 29
<211> LENGTH: 21
<212> TYPE: PRT
<213> ORGANISM: Salmonis sp.

<400> SEQUENCE: 29

Leu Gln Asp Tyr Ser Lys Ser Leu Gly Asp Gly Leu Asp Ile Met Val
 1               5                  10                  15

Asn Lys Met Gly Pro
            20

<210> SEQ ID NO 30
<211> LENGTH: 21
<212> TYPE: PRT
<213> ORGANISM: Oncorhynchus tshawytscha

<400> SEQUENCE: 30

Leu Gln Asp Tyr Ser Lys Ser Leu Gly Asp Gly Leu Asp Ile Met Val
 1               5                  10                  15

Asn Lys Met Gly Pro
            20

<210> SEQ ID NO 31
<211> LENGTH: 21
<212> TYPE: PRT
<213> ORGANISM: Tructa sp.

<400> SEQUENCE: 31

Leu Gln Asp Tyr Ser Lys Ser Leu Gly Asp Gly Leu Asp Ile Met Val
 1               5                  10                  15

Asn Lys Met Gly Pro
            20

<210> SEQ ID NO 32
<211> LENGTH: 22
<212> TYPE: PRT
<213> ORGANISM: Homo sapiens

<400> SEQUENCE: 32

Val Tyr Asp Leu Leu Lys Asp Leu Glu Glu Gly Ile Gln Thr Leu Met
 1               5                  10                  15

Arg Glu Leu Glu Asp Gly
            20

<210> SEQ ID NO 33
<211> LENGTH: 22
<212> TYPE: PRT
<213> ORGANISM: Bovine sp.

<400> SEQUENCE: 33

Val Tyr Glu Lys Leu Lys Asp Leu Glu Glu Gly Ile Leu Ala Leu Met
 1               5                  10                  15

Arg Glu Leu Glu Asp Gly
            20
```

BI-FUNCTIONAL CANCER TREATMENT AGENTS

FIELD OF THE INVENTION

The present invention relates generally to the methodology of preparing and using fusion molecules to treat cancer.

BACKGROUND OF THE INVENTION

Human breast cancer is the predominant malignancy and the leading cause of cancer death in women from Western society, as reported by Miller et al., (eds) BIOLOGY OF FEMALE CANCERS, 31–42 (CRC Press, 1997). According to recent estimation by the American Cancer Society, one in every eight U.S. women will have breast cancer and the disease will kill 43,500 women in 1998.

Several lines of evidence have strongly linked prolactin (PRL) to breast cancer development. It has been reported that the expression level of prolactin receptors (PRLR) is higher in human breast cancer cells compared to normal breast epithelial cells (Reynolds et al., 1997), as well as in surgically removed breast cancer tissues (Touraine, Martini P. et al., *Increased Expression Of Prolactin Receptor Gene In Human Breast Tumors Versus Contiguous Normal Breast Tissues*, (Abstract) 79$^{th}$ Annual Meeting of Endocrine Society, p.113, (1997)). The PRLR levels in malignant breast tissue can be five folds higher over its surrounding normal tissue (see Touraine et al. (1997), supra, making these cells highly sensitive to the stimulation of hPRL. Additionally, it has been suggested that one mechanism of the mitogenic action of estrogen in breast may influence the production and secretion of human prolactin (hPRL), since there is a positive correlation between PRLR, estrogen receptors (ER) or progesterone receptor levels (Sirbasku, 1978; Dixon and Lippman 1986; Lippman an Dickson, 1989). Taken together, these findings lead to a hypothesis that hPRL serves as an autocrine/paracrine growth factor that plays an important role in mammary carcinogenesis (Clevenger, et al., *Am. J. Pathology*, 146:695–705 (1995); Ginsburg, E. et al., *Cancer Res.*, 55:2591–2595 (1995)).

An association between PRL expression and prostate disease has also been proposed in Wennbo et al., *Endocrinol* 138:4410–4415 (1997). PRL receptors are found in prostate tissue as reported Aragona et al., *Endocrinol.* 97:677–684 (1975), and Leake et al., *J. Endocrinol.*, 99:321–328 (1983). In addition,PRL levels has observed that can increase with age (Hammond et al., *Clin. Endocrinol.*, 7:129–135 (1977), Vekemans etal., Br. Med. J. 4:738–739 (1975)) coincident with the development of prostate hyperplasia. Transgenic mice overexpressing the PRL gene developed dramatic enlargement of the prostate gland. (see Wennbo et al. (1977), supra).

In view of its link to both breast and prostate cancer, PRL signaling represents an attractive target for therapeutic intervention. Heretofore, however, no suitable medicaments have been available for this purpose.

Immunological approaches hold great promise in treating cancer. There is ample evidence that cancers express tumor-specific antigen and patients have T cells that can respond to these antigens (Boon, Toward T., *A Genetic Analysis of Human Tumor Rejection Antigens*, Advances in Cancer Research, 58:177–210 (1992); Urban, J L et al., *Tumor Antigens*, Annu. Rev. Immuno. 10:617–644 (1992)). Yet, these T cells, in many instances, are anergic or otherwise ineffective in combating the cancer. Thus far, the main effort in immunological approaches for tumor therapy is to augment weak host immune responses to tumor antigens such as by exogenously administering cytokines to the patients.

Among many cytokines used, interleukin 2 (IL-2) has been demonstrated to have promising results. IL-2 is the principal cytokine responsible for progression of T lymphocytes from the G1 to S phase of the cell cycle (see Morgan et al., *Science* 193:1007–1008 (1979). The principal actions of IL-2 on lymphocytes are as follows: (1) IL-2, as the major autocrine growth factor for T lymphocytes, determines the magnitude of T cell-dependent immune response. (2) IL-2 stimulates the growth of natural killer (NK) cells and enhances their cytolytic effect, as reported in Hendrzak et al., EXPERIMENTAL AND CLINICAL AGENTS, 263–282 *Humana Press Inc.* (1997).

However, it has been reported that cancer patients receiving systemic IL-2 often experience potentially life-threatening side effects that limits the total amount that can be administered which, in turn, directly affects the efficacy of treatment. (see Rosenberg et al., *N. Engl. J. Med.* 319: 1676–1680 (1988); Maas, *Immunobiology* 188: 281–292 (1993)). The main efforts regarding the use of IL-2 in tumor therapy, therefore, have been concentrated on ways and means to balance the side effect and the effective dose i.e., increase the specificity of administered IL-2 (target the IL-2 precisely at the tumor site), thereby dramatically decreasing the side effects induced by high systemic dosage.

Forni G., et al., *J. Immunol.* 138:4033–4041 (1987) demonstrated that injection of a physiological dose of IL-2 directly into tumor caused suppression of their growth. The major advantage of this in situ application is that it decreases toxicity associated with the systemic use of cytokines, but it has the disadvantage of needing to know the exact location of all tumors, which is particularly problematic in patients with widespread metastases.

Further efforts to decrease toxicity have shown that the injection of transfected tumor cells which secrete IL-2 can induce specific T cell-dependent immunity on subsequent challenges by unmodified tumor cells, as reported in Gansbacher et al., *J. Exp. Med.* 172:1217–1224 (1990); Fearon et al., *Cell* 60:397–403 (1990); and Pardoll, D. M., *Immun. Today* 14:310–316 (1993). However, Reisfeld et al., *Curr. Top. Microbiol. Immunol.* 213:27–53 (1996) note that clinical application of such an approach will be both time consuming and costly, since it will involve the isolation, transfection, and re-administration of an individual patient's tumor cells.

Recently, an alternative approach of using the binding specificity of anti-tumor monoclonal antibodies (mAb) to direct cytokines to tumor sites has been introduced. See Reisfeld et al.(1996), supra. This approach combines the unique targeting ability of a mAb with the multifunctional activities of cytokines, therefore, achieving an effective concentration of IL-2 in the tumor microenviroment. Targeted IL-2 therapy can completely eradicate disseminated pulmonary and hepatic murine melanoma metastases in immunocompetent, syngeneic mice, as shown in Gillies et al., *Proc. Natl. Acad. Sci. USA* 89:1428–1432 (1992); and Sabzevari et al., *Proc. Natl. Acad. Sci. USA* 91:9626–9630 (1994).

There are advantages of this targeted IL-2 therapy. For instance, this therapy does not require the mAb-IL-2 fusion protein to reach all target cells to achieve the maximum effects as in the case of other mAb targeted therapies since it is not a direct cytotoxic reaction. Reisfeld et al. (1996), supra. Most importantly, the therapeutic effect of targeted IL-2 therapy is associated with the induction of a long-lived and transferable, protective tumor immunity. This mAb targeted IL-2 therapy is also different and advantageous from ex vivo transfer of cytokine genes, since it concentrates IL-2 in the tumor environment in a non-personalized, making this approach more clinically feasible.

Although the targeted immunotherapy approach shows promise in treating cancer, the therapeutic benefits of combining the effects of antagonizing PRL and targeted IL-2 is unknown in treating cancer. There is, therefore, an unmet need to develop agents and therapies for simultaneously antagonizing the role of PRL in cancer maintenance or proliferation and augmenting the patient's immune response to the cancer.

SUMMARY OF THE INVENTION

Accordingly, it is an object of the invention to provide a medicament that is capable of interfering with the prolactin signaling mechanism in a cancer cell.

It is yet another object of the invention to provide a medicament that induces apoptosis in a cancer cell.

It is a further object of the invention to provide a medicament that contains a receptor antagonizing domain and a positive immunomodulating domain.

It is still another object of the invention to provide a method for treating a patient suffering from cancer by simultaneously antagonizing a receptor present in a targeted cancer cell and augmenting the patient's immune response to the cancer.

It is another object of the invention to provide a method of treating cancer by employing the medicaments described herein.

These and other objects which will be more readily apparent upon reading the following disclosure may be achieved by the present invention.

In a composition of matter aspect, the present invention relates to substantially to a protein comprising a receptor antagonizing domain and a positive immunomodulator domain. The invention further provides that the receptor antagonizing domain can be an apoptosis-promoting domain, while the positive immunomodulator domain can be an interleukin. The receptor antagonizing domain also can be the amino acid sequence SEQ ID NO: 34 or conservative variants thereof.

In a methodological aspect, the present invention relates to a method for treating cancer, comprising administering to a patient an effective amount of a protein having a receptor-antagonizing domain and a positive immunomodulator domain. The invention further provides a methodology for administering to a patient any of the proteins described herein.

DETAILED DESCRIPTION OF THE PREFERRED EMBODIMENTS

Figure 1:
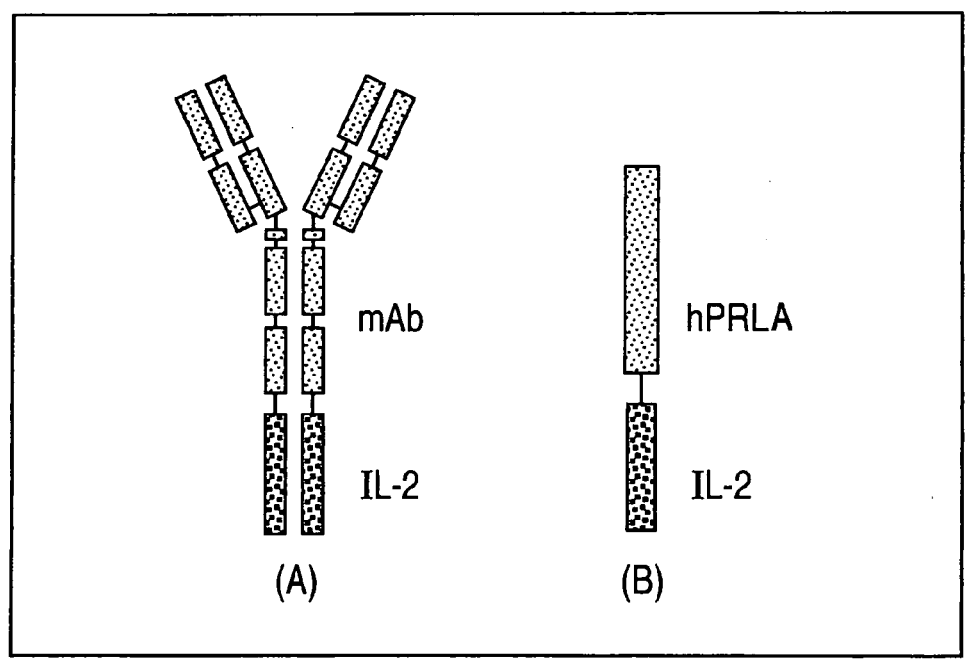
FIG. 1 is a schematic representation of an inventive bi-functional molecule. (A) mAb-IL-2 fusion protein model proposed in previous studies by Reisfeld et al. (1996), supra and (B) hPRLA-IL-2 fusion protein according to the invention.

It has been discovered by the present inventors that the combined effects of endocrine-based and targeted cytokine therapies greatly enhance the treatment of cancer. For instance, products and methods of treatment herein disclosed act to inhibit the autocrine/paracrine effects of endogenous PRL by blocking the PRLR, typically resulting in apoptosis. In addition, this approach positively modulates an immune response, thereby inducing tumor-specific T lymphocyte cytotoxicity specifically at the malignant tissue.

As used herein, "apoptosis" refers to a process whereby developmental or environmental stimuli activate a genetic program to implement a specific series of events that culminate in the death and efficient disposal of a cell. The morphological changes in the cell include dramatic shrinkage of cell volume, accompanied by dilation of endoplasmic reticulum and convolution of the plasma membrane. In turn, this causes the cell to break up into a series of membrane-bounded bodies, containing structurally normal, yet compacted, organelles. The nucleus undergoes discontinuous chromatin condensation and nuclease-mediated DNA fragmentation occurs, degrading chromosomal DNA into small oligonucleosomal fragments. The nucleus and cytoplasm condense and the dying cell ultimately fragments into membrane-bound apoptotic bodies that are rapidly phagocytosed and digested by macrophages or by neighbouring cells.

The present invention combines the benefits associated with blocking the PRLR and positively modulating an immune response by utilizing a multi-domain molecule, each domain having the ability to carry out one of these functions. Typical molecules have a "receptor-antagonizing domain" or an "apoptosis-promoting domain," combined with a "positive immunomodulator domain."

As used herein, a "receptor-antagonizing domain" is a ligand that specifically binds to a receptor that is associated with a disorder like cancer, whereupon binding to the receptor, the receptor-antagonizing domain acts to inhibit one or more cellular processes, thereby interrupting the etiology or maintenance of the disease. Such a domain that induces apoptosis is herein referred to as the "apoptosis-promoting domain," while a "positive immunodulator domain" is one that augments an immune response, preferably enhancing the immune response against an abnormal cell, like a cancer cell. Such an immune response typically involves recruiting T-cells and enhancing their, for example, cytotoxic function.

The benefits of a fusion protein having these characteristics are immense. For example, carcinogenic tissues are often characterized by increased levels of one or more protein receptors. A fusion protein containing a domain that is specific to one of these receptors will be able to specifically target the cancer tissue. Where the receptor antagonizing domain disrupts the etiology of the cancer, or disrupts cancer maintenance, as is the case of an apoptosis-promoting domain, the receptor antagonizing portion of the molecule has a direct therapeutic effect. In addition, due to the presence of the positive immunomodulator domain, the molecule has a secondary therapeutic effect by inducing the patient's own immune system to respond specifically against the diseased tissue.

Accordingly, candidates to receive the therapy according to this invention include individuals who suffer from malignant tumors those of which are characterized by the presence of at least one receptor related to tumor maintenance or proliferation. In a preferred embodiment, the receptor-antagonizing domain of the fusion protein is an apoptosis-promoting domain, which binds to a targeted membrane-bound receptor. Such binding induces apoptosis; simultaneously, the positive immunomodulator domain induces tumor-specific recruitment and enhancement of T lymphocyte cytotoxicity.

The Inventive Bi-Functional Protein:

In accordance with the invention, bi-functional proteins are contemplated that have unique dual therapeutic effects on malignant tissue, namely (a) receptor-antagonizing and/or apoptosis-promoting (which may be one and the same) and (b) positive immunomodulating. The invention also contemplates nucleic acids (e.g. DNA or RNA) encoding the inventive bi-functional proteins.

Receptor-antagonizing Domain

The invention contemplates a first domain that, in one aspect, will localize the effects of the positive immunomodulator domain to the diseased tissue. For example, carcinogenic tissues are often characterized by increased levels of one or more protein receptors. A fusion protein containing a domain that is specific to one of these receptors will be able to specifically target the cancer tissue, resulting in a localized tumor cytotoxicity reaction directed to the targeted tissue.

In one embodiment, the domain that targets a particular receptor site is a receptor-antagonizing domain, which, as its name suggests, binds to and antagonizes its cognate receptor. In a preferred embodiment, the receptor-antagonizing domain is an apoptosis-promoting domain. This targeted therapy approach, utilizing a receptor antagonizing domain, is designed to provide dramatically decreased systemic concentrations of the positive immunomodulator domain (e.g., IL-2), thereby reducing its toxicity in vivo.

An additional therapeutic benefit of this dual-function molecule is that the receptor-antagonizing domain typically has endocrine-blocking ability. Thus, where the receptor-antagonizing domain, for example, is a prolactin antagonist, the normal endocrine function of prolactin will be disrupted. As a consequence of this endocrine-blocking, in the case of prolactin and similar molecules, for instance, apoptosis of the targeted cells can result. In that case, the receptor-antagonizing domain is also an apoptosis-promoting domain.

In the case of an apoptosis-promoting domain, such a domain generally is designed by creating antagonists of the normal function of a cellular component that is involved in preventing apoptosis. In both breast and prostrate cancer tissue, for example, carcinogenesis and malignant cell proliferation is stimulated, at least in part, by increased levels of PRLR. Signaling via the PRLR is known to be mediated by dimerization of the prolactin receptor, which is itself mediated by dimerization of receptor-bound prolactin molecules. The binding of endogenous PRL to two PRLRs induces PRLR dimerization, thereby triggering signal transduction into the cancer cells. Accordingly, one embodiment of the invention entails antagonizing the normal apoptosis-inhibiting function of prolactin using a prolactin antagonist (PRLA) (i.e., a prolactin antagonist domain).

Signal transduction in the PRLR signaling pathway involves signal transducers and activators of transcription (STAT) phosphorylation, which is involved in preventing or blocking apoptosis, the normal result of PRLR agonism. Thus, G129R antagonist promotes apoptosis by inhibiting STAT 5 phosphorylation in human breast cancer cells. Accordingly, blocking the PRLR inhibits the autocrine/paracrine effects of endogenous PRL, which involves STAT 5, and results in apoptosis. Thus, one class of apoptosis-promoting compounds contemplated by the invention is one that can inhibit STAT 5 phosphorylation.

A suitable PRLA contemplated by the invention generally will retain the characteristic of specific binding to the PRLR, yet will have some structural deficiency that disrupts the normal PRL apoptosis-blocking mechanism. Such a structural deficiency includes those that disrupt PRL(and thus PRLR) dimerization.

Figure 3:
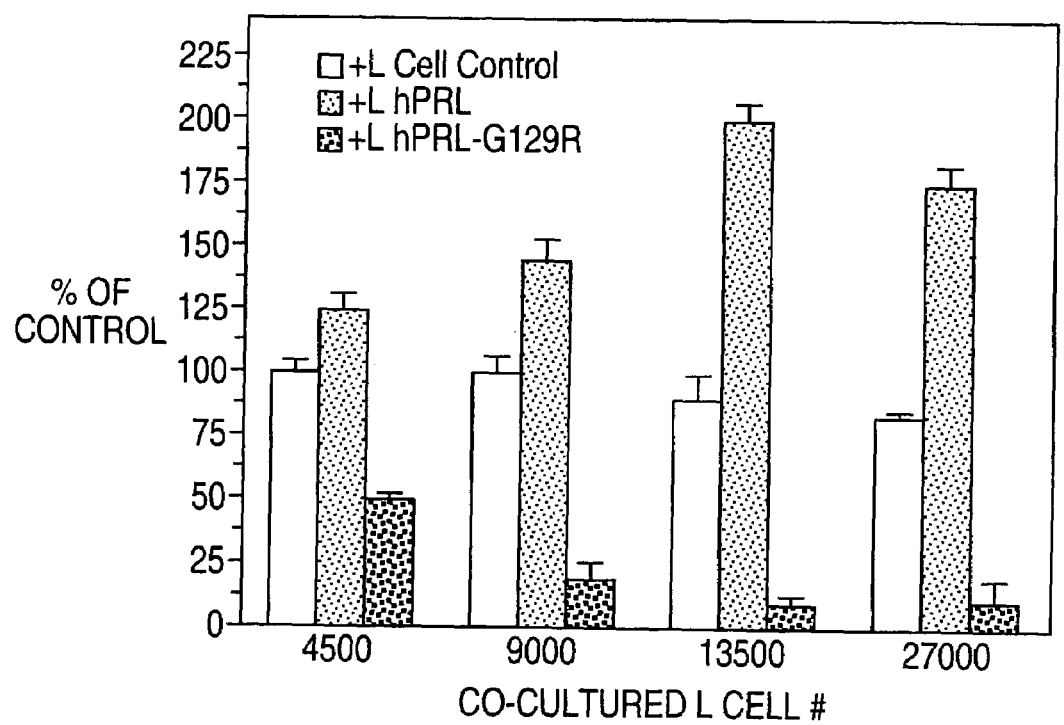
FIG. 3 illustrates the dose-response inhibitory effects of hPRI-G129R and stimulatory effects of hPRL in T-47D human breast cancer cells using co-culture method. The x-axis represents the co-cultured L cell (control, L-PRL or L-hPRL-G129R cell numbers. Each data point represents a mean of at least three independent experiments with triplicate wells.
Figure 4:
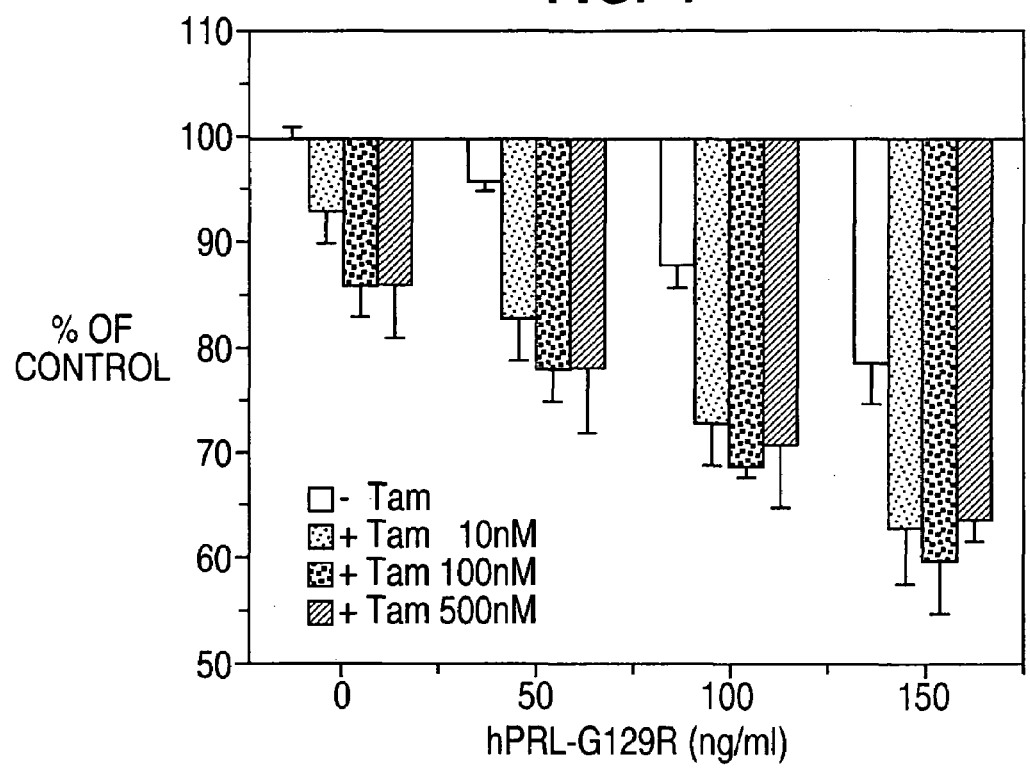
FIG. 4 shows the dose-response inhibitory effects of hPRL-G129R and its additive effects with 4-OH-Tamoxifen in T-47D human breast cancer cell proliferation assay. The x-axis represents the hPRL-G129R concentration either in the absence (open bars) or presence of 4-OH-Tamoxifen. Each data point represents a mean of at least three independent experiments with triplicate wells.

In one preferred embodiment, shown in SEQ ID NO: 34, this structural deficiency is a substitution of Gly to Arg at a position corresponding to 129 in hPRL (denoted as hPRL-G129R). FIGS. 3 and 4, as well as the cell-based assays presented in Examples 4, 5 and 6 demonstrate that this mutated hPRL acts as a true hPRLR antagonist. Accordingly, a receptor-antagonizing domain such as hPRL-G129R can serve as a therapeutic medicament for treating certain types of cancer.

This embodiment is supported by Chen et al., *Clin. Can. Res.* 5:3583–93 (1999), who disclose a species comparison of amino acid sequences within the third α-helical region of PRLs, shown in Table 1.

TABLE 1

| Species | Domain | Peptide Sequence | 129 | Pep. Seq. |
|---|---|---|---|---|
| Human | PRL | IEEQTKRLLR | G | MELIVS-QVHP |
| Rat | PRL | IEEQNKRLLE | G | IEKIIG-QAYP |
| Mouse | PRL | IEEQNKQLLE | G | VEKIIS-QAYP |
| Hamster | PRL | IGEQNKRLLE | G | IEKTLG-QAYP |
| Fin whale | PRL | EEEENKRLLE | G | MEKIVG-QVHP |
| Mink | PRL | IEEENRRLLE | G | MEKIVG-QVHP |
| Cattle | PRL | IEEQNKRLIE | G | MEMIFG-QVIP |
| Sheep | PRL | EEEENKRLLE | G | MENIFG-QVIP |
| Pig | PRL | IEEQNKRLLE | G | MEKIVG-QVHP |
| Camel | PRL | IEEQNKRLLE | G | MEKIVG-QVHP |
| Horse | PRL | EIEQNRRLLE | G | MEKIVG-QVQP |
| Elephant | PRL | VKEENQRLLE | G | IEKIVD-QVHP |
| Ancestral mammal | PRL | IEEENKRLLE | G | MEKIVG-QVHP |
| Chicken | PRL | IEEQNKRLLE | G | MEKIVG-RVHS |
| Turkey | PRL | IEEQDKRLLE | G | MEKIVG-RIHS |

TABLE 1-continued

| Species | Domain | Peptide Sequence | | 129 Pep. Seq. |
|---|---|---|---|---|
| Sea turtle | PRL | IEEQNKRLLE | G | MEKIVG-QVHP |
| Crocodile | PRL | IEEQNKRLLE | G | MEKIIG-RVQP |
| Alligator | PRL | IEEQNKRLLE | G | MEKVIG-RVQP |
| Ancestral amniote | PRL | IEEQNKRLLE | G | MEKIVG-QVHP |
| Xenopus | PRL | VEEQNKRLLE | G | MEKIVG-RIHP |
| Bullfrog | PRL | VEEQTKRLLE | G | MERIIG-RIQP |
| Lungfish | PRL | VEDQTKQLIE | G | MEKILS-RMHP |
| Tllapia | PRL | MQQYSKSLKD | G | LD-VLSSKMGS |
| Tilapia | PRL | MQEHSKDLKD | G | LD-ILSSKMGP |
| Common carp | PRL | LQENINSLGA | G | LEHVP-NKMDS |
| Bighead carp | PRL | LQDNINSLGA | G | LERVV-HKMGS |
| Silver carp | PRL | LQDNINSLVP | G | LEHVV-HKMGS |
| Chun salmon | PRL | LQDYSKSLGD | G | LD-IMVNKMGP |
| Chinook salmon | PRL | LQDYSKSLGD | G | LD-IMVNKMGP |
| Trout | PRL | LQDYSKSLGD | G | LD-IMVNKMGP |
| Human | GH | VYDLLKDLEE | G | IQTLMRELEDG |
| Bovine | GH | VYEKLKDLEE | G | ILALMRELEDG |

According to Table 1, it is clear that Gly 129 of hPRL is invariable among PRLs, suggesting an important role in its function. Thus, substituting any amino acid for Gly 129 should produce PRLA in each of these species (Chen et al., *Molec. Endocrinol.* (1995)). In one embodiment, an antagonist is created by substituting a relatively bulky side chain amino acid, such as Arg for Gly 129. Accordingly, one aspect of the invention contemplates conservative variants of PRL that are characterized by the presence of a relatively small side-chain amino acid (i.e. Gly) at a specific position, such that substituting the small side-chain amino acid for a bulky side-chain amino acid will result in an antagonistic form of the protein.

The receptor-antagonizing domain of present invention also includes conservative variants of receptor antagonizing domains discussed herein. The overall structure and composition of the inventive domains, in that respect, are important only insofar as they confer the appropriate functional characteristics, i.e., receptor antagonism, apoptosis induction, positive immunomodulation.

Conservative variants according to the invention generally conserve the overall molecular structure of the protein domains. Given the properties of the individual amino acids comprising the disclosed protein products, some rational substitutions will be apparent. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)–(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Conservative variants specifically contemplate truncations of the presently described receptor antagonizing domains. Truncations may be made from the N- or C-terminus, but generally do not entail deleting more than about 30% of the native molecule. More preferably, less than about 20%, and most preferably, less than about 10%, of the native molecule is deleted.

In general, both the DNA and protein molecules of the invention can be defined with reference to "sequence identity." Some molecules have at least about 50%, 55% or 60% identity. Preferred molecules are those having at least about 65% sequence identity, more preferably at least 65% or 70% sequence identity. Other preferred molecules have at least about 80%, more preferably at least 80% or 85%, sequence identity. Particularly preferred molecules have at least about 90% sequence identity, more preferably at least 90% sequence identity. Most preferred molecules have at least about 95%, more preferably at least 95%, sequence identity. As used herein, two nucleic acid molecules or proteins are said to "share significant sequence identity" if the two contain regions which possess greater than 85% sequence (amino acid or nucleic acid) identity.

"Sequence identity" is defined herein with reference the Blast 2 algorithm, which is available at the NCBI, (ww.ncbi.nlm.nih.gov/Blast), using default parameters. References pertaining to this algorithm include: those found at www.ncbi.nlm.nih.gov/BLAST/blast references.html Altschul, S. F., Gish, W., Miller, W., Myers, E. W. & Lipman, D. J. (1990) "Basic local alignment search tool." J. Mol. Biol. 215:403–410; Gish, W. & States, D. J. (1993) "Identification of protein coding regions by database similarity search." Nature Genet. 3:266–272; Madden, T. L., Tatusov, R. L. & Zhang, J. (1996) "Applications of network BLAST server" Meth. Enzymol. 266:131–141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402; and Zhang, J. & Madden, T. L. (1997) "PowerBLAST: A new network BLAST application for interactive or automated sequence analysis and annotation." Genome Res. 7:649–656. Accordingly, the prolactin peptide sequences from different species, which include those listed in Table 1, can be aligned, using standard computer programs like BLAST, to inform further variation in prolactin-derived receptor-antagonizing domains that preserve their essential function.

In addition to proteins that are conservative variants of those disclosed herein, the invention also contemplates the use of proteins that play a role in inducing tumor proliferation, wherein an amino acid substitution will inhibit the protein's ability to induce this proliferation. For example, Gly 119 and Gly 120 of bovine growth hormone (bGH) and hGH, respectively, play critical roles in the action of GH in stimulating growth enhancement. Growth hormone receptor (GHR) dimerization is thought to be a key step for HG signal transduction. Accordingly, any amino acid substitution (other than Ala), especially one with a bulky side chain such as Arg at these respective positions will prevent receptor dimerization, resulting in a growth hormone antagonist (GHA). Thus, antagonists such as GHA are contemplated by the invention.

In addition to antagonizing the normal function of a cellular component involved in preventing apoptosis, the invention further comprehends, in the context of apoptosis-promoting domains, agents that induce apoptosis by positive means. That is, such agents do not work by antagonizing an anti-apoptotic pathway; rather they induce an apoptotic pathway. Examples of such agents are protein kinase C (PKC) inhibitors, including chelerythrine.

The benzophenanthridine alkaloid chelerythrine (1,2-dimethoxy-12-methyl[1,3]benzodioxolo[5,6-c]phenanthridinium; $C_{21}H_{18}NO_4$), also known as toddaline, is extractable either in pure form or as a mixture with other benzophenanthridine alkaloids from *Chelidonium majus* L., *Zanthoxylum simulans, Sanguinaria candensis* (or bloodroot), *Macleaya cordata, Carydali sevctocozii, Carydali ledebouni, Chelidonium majusm* and other members of Papaveracaceae.

Inhibitors of PKC can interact with the substrate binding site (ATP or protein) or with the regulatory domain where activation occurs (diacylglycerol or phorbol ester binding site). Chelerythrine interacts directly with the catalytic domain of PKC. It is one of the most potent inhibitors of PKC identified and does not appear to inhibit any other protein kinases. For example, chelerythrine shows potent cytotoxic effects against L-1210 tumor cells with an IC50 value of 0.053 µM by inhibiting cell growth and differentiation, as discussed by Herbert et al., *Bioechem. Biophys. Res. Commun.* 172:993 (1990). Chelerythrine induces apoptosis by specifically inhibiting PKC in a concentration-dependent manner and strongly inhibiting platelet aggregation induced by strong aggregation inducers, such as arachidonic acid and collagen.

Thus, upon introduction to tumor cells, chelerythrine chloride can decrease the apoptotic threshold and trigger apoptosis therein. This is particularly true when chelerythrine therapy is used in conjunction with other methods of treatment. Accordingly, a fusion molecule that includes chelerythrine fused to another molecule used to combat cancer, for example a positive immunomodulator domain, is contemplated by the invention. A molecule containing chelerythrine can be fused to another molecule (i.e. a domain as described herein) by conventional chemical means, using multifunctional cross-linkers, for example. Protein-based PKC inhibitors may be made as fusion proteins.

Positive Immunomodulator Domain

The invention also contemplates an additional, yet separate, domain that acts as a positive immunomodulator. Preferred immunomodulator domains support a tumor-directed positive immune response. An example of a suitable positive immunomodulator includes a cytokine that can recruit T lymphocytes to the tumor, thereby inducing tumor specific T lymphocyte cytotoxicity at the malignant tissue. In a preferred embodiment, the positive immunomodulator is IL-2, which is characterized by its ability to control the magnitude of T cell-dependent immune response. IL-2 also has activity on microphages and monocytes. In addition, IL-2 stimulates the growth of natural killer (NK) cells and enhances their cytolytic effect.

In addition to IL-2, the invention contemplates other molecules, including additional cytokines, having these or similar properties. For example, IL-12 can represent the positive immunomodulator domain. IL-12 is a key cytokine for directing the T cell response to that of a Th1 type. IL-12 is made by B cells and monocytes/macrophages and acts synergistically with IL-2 to induce IFNγ production by T cells and NK cells. It also enhances the cytotoxicity activity of both T cells and NK cells. The invention also includes conservative variants (as detailed above) of the aforementioned positive immunomodulator domains.

Other suitable candidates for the positive immunomodulator domain include the interferons (IFN). For example, IFN-β, by itself, is known to inhibit tumor cell proliferation. IFN-β is a universal macraphage activating agent for antitumor activity. Accordingly, a fusion molecule containing IFN-β bound to an apoptosis promoting domain would provide localized positive immunomodulating therapy to a targeted tissue.

Figure 2:
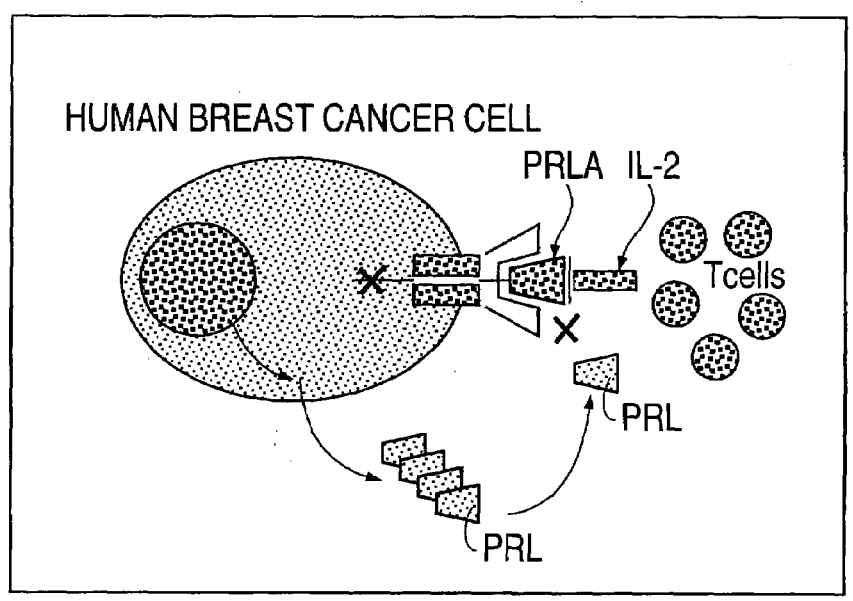
FIG. 2 is a schematic representation of a proposed mechanism of action for an inventive bi-functional fusion protein. PRL produced by breast cancer cell is prevented from reaching the PRLR due to the occupancy of the fusion protein (PRLA). At the same time, IL-2 portion of the fusion protein stimulates the anti tumor T cell reaction.

Preparing Exemplary Bi-Functional Molecules:

A bi-functional protein contemplated by this invention is one that contains each of the previously mentioned domains, namely receptor-antagonizing (which also may be apoptosis-promoting) and positive immunomodulating, wherein upon such fusing, both domains substantially retain their associated characteristics, independent of the other. FIG. 2 discloses one embodiment of the invention, according to these characteristics. Although typically produced as fusion proteins, the domains also may be fused by conventional chemical means, using multifunctional cross-linkers, for example. When fusion proteins are made, either domain may be placed C-terminal or N-terminal to the other.

Figure 5:
FIG. 5 is a schematic representation of cloning and construction of the expression plasmid of pUCIG-MT-hPRLA-IL-2 fusion protein cDNA.
Figure 5:
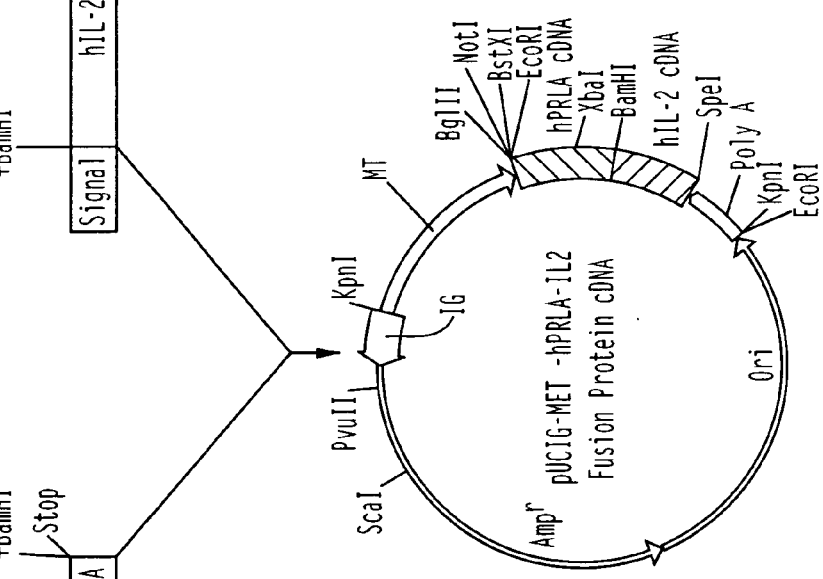

In one embodiment, the fusion protein is a hPRLA-IL-2 protein, as shown in FIG. 1. This fusion protein can be integrated into an expression vector, as shown in example 1 and FIG. 5. The generated expression vector can then be transfected into a stable cell line to subsequently produce a purified protein. Examples 2 and 3 are non-limiting procedures for carrying out the vector transformation and purification processes. This fusion protein has the C-terminus of PRLA fused to the N-terminal side of IL-2, which is shown in FIG. 5. However, the invention also contemplates any fusion protein having domains as described herein.

Suitable methods for creating the fusion protein should be ones that do not substantially change the biological activity of either of these domains. For example, it has been demonstrated that fusion of the N-terminal of IL-2 to the C-terminal end of an antibody does not change the biological activity of IL-2 Reisfeld et al. (1996), supra. Therefore, a similar strategy can be adopted to produce a fusion protein according to the invention. This process includes designing a cDNA encoding a fusion protein which links the N-terminus of the positive immunomodulator domain to the C-terminus of receptor-antagonizing domain.

There is evidence, moreover, that the C-terminal ends of hGH (we deleted up to 10 amino acids) are not important for growth promoting activities in transgenic mice (Chen et al., 1993) and, based on structural similarity, fusion of a positive modulator to the C-terminal end of other receptor-antagonizing domains, such as hPRLA, should not alter the binding affinity of these domains.

The present invention is not limited to any particular method of producing the desired fusion protein contemplated herein. According to the contemplated recombinant methods of production, however, the invention provides recombinant DNA constructs comprising one or more of the nucleotide sequences of the domains described in the present invention. The recombinant constructs of the present invention comprise a vector, such as a plasmid or viral vector, into which a DNA or DNA fragment, typically bearing an open reading frame, is inserted, in either orientation. The invention further contemplates cells containing these vectors.

Recombinant protein production is well known in the art and is outlined briefly below.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include E. coli, Bacillus subtilis, Salmonella typhimurium and various species within the genera Pseudomonas, Streptomyces, and Staphylococcus, although others may, also be employed as a matter of choice. In a preferred embodiment, the prokaryotic host is E. coli.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotec, Madison, Wis., USA), pBs, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia). A preferred vector according to the invention is THE Pt7I expression vector (Paris et al., *Biotechnol. Appl. Biochem.* 12:436–449 (1990)).

These "backbone" sections are combined with an appropriate promoter and the structural sequence to be expressed. Bacterial promoters include lac, T3, T7, lambda $P_R$ or $P_L$, trp, and ara. T7 is the preferred bacterial promoter.

Following transformation of a suitable host strain and growth of the host strain to an appropriate cell density, the selected promoter is derepressed/induced by appropriate means (e.g., temperature shift or chemical induction) and cells are cultured for an additional period. Cells are typically harvested by centrifugation, disrupted by physical or chemical means, and the resulting crude extract retained for further purification.

Eukaryotic Expression

Various mammalian cell culture systems can also be employed to express recombinant protein. Examples of mammalian expression systems include selected mouse L cells, such as thymidine kinase-negative (TK) and adenine phosphoribosul transferase-negative (APRT) cells. Other examples include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, early and late SV40, LTRs from retrovirus, and mouse metallothionein-1. Exemplary mammalian vectors include pWLneo, pSV2cat, pOG44, pXT1, pSG (Stratagene) pSVK3, pBPV, pMSG, and pSVL (Pharmacia). In a preferred embodiment, the mammalian expression vector is pUCIG-MET. Selectable markers include CAT (chloramphenicol transferase).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts. (E.g., See Logan et al., 1984, *Proc. Natl. Acad. Sci. USA* 81:3655–3659).

Therapeutic Compositions:

The proteins of the present invention can be formulated according to known methods to prepare pharmaceutically useful compositions, whereby the inventive molecules, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). In order to form a pharmaceutically acceptable composition suitable for effective administration, such compositions will contain an effective amount of one or more of the proteins of the present invention, together with a suitable amount of carrier vehicle.

Pharmaceutical compositions for use in accordance with the present invention may be formulated in conventional manner using one or more physiologically acceptable carriers or excipients. Thus, the bi-functional molecules and their physiologically acceptable salts and solvate may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the composition may take the form of tablets or lozenges formulated in conventional manner.

For administration by inhalation, the bi-functional molecules for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The bi-functional proteins may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the bi-functional molecules may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The compositions, since they are useful in cancer treatment, may be formulated in conjunction with conventional chemotherapeutic agents. Conventional chemotherapeutic agents include alkylating agents, antimetabolites, various natural products (e.g., vinca alkaloids, epipodophyllotoxins, antibiotics, and amino acid-depleting enzymes), hormones and hormone antagonists. Specific classes of agents include nitrogen mustards, alkyl sulfonates, nitrosoureas, triazenes, folic acid analogues, pyrimidine analogues, purine analogs, platinum complexes, adrenocortical suppressants, adrenocorticosteroids, progestins, estrogens, antiestrogens and androgens. Some exemplary compounds include cyclophosphamide, chlorambucil, methotrexate, fluorouracil, cytarabine, thioguanine, vinblastine, vincristine, doxorubincin, daunorubicin, mitomycin, cisplatin, hydroxyurea, prednisone, hydroxyprogesterone caproate, medroxyprogesterone, megestrol acetate, diethyl stilbestrol, ethinyl estradiol, tomoxifen, testosterone propionate and fluoxymesterone. In treating breast cancer, for example, tamoxifen is particularly preferred.

Methods of the Invention:

Treatment Methods

The inventive therapeutic methods according to the invention generally utilize the bi-functional proteins identified above. The domains of the fusion proteins share the ability to specifically target a specific tissue and/or augment an immune response to targeted tissue. A typical method, accordingly, involves binding a receptor of a targeted cell to the receptor-antagonizing domain of the fusion protein and/or stimulating a T-cell dependent immune response via the positive immunomodulator domain.

Therapeutic methods involve administering to a subject in need of treatment a therapeutically effective amount of a fusion protein. "Therapeutically effective" is employed here to denote the amount of fusion proteins that are of sufficient quantity to inhibit or reverse cancer growth (e.g., induce apoptosis). Some methods contemplate combination therapy with known cancer medicaments or therapies, for example, chemotherapy (preferably using compounds of the sort listed above) or radiation. The patient may be a human or non-human animal. A patient typically will be in need of treatment when suffering from a cancer characterized by increased levels of receptors that promote cancer maintenance or proliferation.

Administration during in vivo treatment may be by any number of routes, including parenteral and oral, but preferably parenteral. Intracapsular, intravenous, intrathecal, and intraperitoneal routes of administration may be employed, generally intravenous is preferred. The skilled artisan will recognize that the route of administration will vary depending on the disorder to be treated.

Determining a therapeutically effective amount of the bi-functional protein, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484–528 (Mack Publishing Company 1990).

Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the induction or substantial induction of T lymphocyte cytotoxicity at the targeted tissue or a decrease in mass of the targeted tissue. Suitable dosages can be from about 1 mg/kg to 10 mg/kg.

Screening Assays to Determine the Biological Activities of the Fusion Protein

The present invention also provides cell-based assay systems that can be used to compare the biological activities of the apoptosis-promoting domain, positive immunomodulating domain, and/or a fusion protein comprising each of these domains. To this end, a cell proliferation assay is used to ensure that the fused domains of the fusion protein each retain a function similar to the respective domain when it is not fused (i.e. not part of a fusion protein).

In one embodiment, the biological activity of the fusion protein will be determined by introducing the protein to two separate types of cell lines in vitro: each cell line determining the activity of a specific domain. For example, a cell line that is a reliable indicator of the biological activities of the apoptosis-promoting domain should be used to test the effects of that domain, while a cell line capable of indicating positive immunomodulating domain should be used to monitor the activity of the other domain.

By introducing to a cell line various concentrations of a particular domain in its antagonized, non-antagonized, and fused forms, one of skill in the art could determine the biological activity of the apoptosis-promoting domain of the fused protein vis-à-vis the same domain in its non-fused state. There are numerous ways to measure apoptosis. These methods include, but are not limited to the following techniques: (1) *Loss of cell viability*—measured by a failure to either exclude vital dye or uptake MTT (3-(4,5-dimethylthiazol-2-yl)-2,5-diphenyltetrazolium bromide), or MTS-PMS; (2) *DNA fragmentation*—assayed by agarose gel electrophoresis, PFG electrophoresis, in situ terminal transferase labelling (TUNEL); *Cell and nuclear morphology*—employing microscopy to visualize chromatin condensation, DNA organization, and cytoplasmic integrity; and *Cysteine protease activation assays*—utilizing caspase activation assays combined with colorimetric or fluorescent readouts, poly (ADP-ribose) polymerase (PARP) or laminin cleavage by western blot or immunohistochemisrty.] Examples 4 and 9, which use a human breast cancer cell line (T-47D), provide non-limiting examples of acceptable assay systems to this extent.

Likewise, a cell line that can measure activity of the positive immunomodulating domain should be similarly used to monitor the activity of this domain of the fusion protein. Example 9, which uses a murine T cell line (HT-2), is one possible, yet non-limiting method to determine biological activity of the positive immunomodulating domain in the fusion protein.

Another preferred method for determining activity of the fusion protein according to the invention is the conduct tests in vivo. A suitable host for this test would be a mammalian host containing cancer tissue capable of binding the apoptosis-promoting domain of the fusion protein. A suitable control can be any cell line characterized by few or no receptor sites for the chosen apoptosis-promoting domain. Example 10 provides a non-limiting example of an in vivo study, using mouse cells.

The following examples are intended to be illustrative and not limiting

EXAMPLES

Example 1

Cloning and Construction of the Expression Plasmid pUCIG-MT-Hprla-IL2 Fusion Protein cDNA.

PCR fragments from hPRLA cDNA (from restriction site Xbal to the sequence just before translational stop codon) and IL-2 cDNA (purchased from ATCC) from amino acid sequence +1 site to translational stop codon, respectively, were separately amplified. Next, these fragments were ligated into pUCIG-MET, a mammalian expression vector, to generate an expression vector that has incorparated these fragments (i.e. pUCIG-MET-hPRLA-IL2). A BamH1 restriction site was added for cloning purposes between hPRLA and IL-2 cDNA, which resulted in two extra amino acid residues (Gly and Ser) at the junction of the fusion protein.

Example 2

Transfecting an Expression Plasmid into a Stable Cell Line.

We have already generated hPRL-IL-2, and hPRLA-IL-2 pooled stable mouse cells for our preliminary in vitro studies. In producing a fusion protein according to this invention, mouse L cells are used. These cells are first co-transfected with DNA molecules encoding hPRLA-IL-2 cDNA driven by mouse metallothionien regulatory sequence, along with the herpes viral TK gene and the hamster APRT gene (Leung et al., 1985) by using lipofectin method (Gibco BRL, Gaithersburg, Md.). Following double selection for the TK +, the APRT+phenotypes, stable hPRL or hPRL analog-secreting mouse L cell lines are established and maintained in Dulbecco Modified Eagles Medium (DMEM, Gibco BRL, Gaithersburg, Md.) plus 10% Nu-serum (Collaborative Research, Bedford, Mass.), 15 μg/ml hypoxanthine, 15 μg/ml aminopterin, 15μg/ml thymidine and 50 μg/ml gentamicin. Cells are passed into T150 flasks until they reach 90% confluency. At that point, serum free conditioned media is collected every 24 hours and pooled. Pooled medium is frozen at −20 C. until further purification is accomplished.

Example 3

Purifying the Fusion Protein.

To obtain an increased yield of fusion proteins, it is desired to first purify them, according to procedures that are well known in the art. These steps include: removing the cells from culture via centrifugation, followed by precipitation, crossflow ultrafiltration, and chromatography methodologies, such as low pressure SEC and preparative RP-HPLC chromatography. These steps are followed by: buffer exchange, depyrogenation, and lyophilation.

Step One: Cell Removal —80–100% of the conditioned medium is centrifuged at 6000×g for 30 min and at 4° C. The starting cell culture medium has a volume of 80–100 liters. All the hPRL-G129R is recovered in this step.

Step Two: Precipitation—The precipitation procedure is carried out by gradually adding 3.5 kg ammonium sulfate to 10 liters of cell culture medium with constant stirring. The solution is placed at 40° C. for 12 hours. The supernatant is centrifuged off. The precipitate is then dissolved in 2 liters of distilled water. The non-dissolved impurities are removed by centrifugation. All the centrifugation steps are operated at 6000×g for 30 min and at 4° C. The final volume of solution is about 5 liters.

Step three: Volume Reduction using Crossflow Ultrafiltration—A 10 K molecular cut-off membrane in a 2000 ml stirred cell is used to reduce the volume of the solution, so that it reaches 10% of the bed volume of the SEC size-exclusive column. This membrane filtration step is operated at 55 psi.

Step four: Low Pressure SEC—The purpose of this low pressure SEC step is to remove the large size impurities and small size impurities that may contaminate the preparative RP-HPLC column. Low pressure SEC is performed in a 44×1000 mm Amicon glass column packed with Bio-Rad P60 gel. The bed volume of the gel is 1231 ml. 0.05M ammonium sulfate is flowed through the column at a flow rate of 0.5 ml/min. The entire setup is placed in a refrigerator and maintained at 4° C.

Step five: Preparative RP-HPLC—In this work, a Waters (Millipore Corp., Bedford, Mass.) preparative HPLC system with a UV-visible detector is used. A preparative- scale Dynamax C, RP-BPLC column (21.4×250 mm, 5 gm, 300A pore size) from Rainin Instrument, Inc. (Woburn, Mass.) is used to obtain the hPRL-G129R product with high purity. A linear gradient, from 40% acetonitrile (ACN) (v/v) +0.1% trifluoroacetic acid (TFA) to 80% ACN +0.1% TFA, was used to achieve the separation. The linear gradient is established over 60 min, and the mobile phase flow rate is 5 ml/min. The UV detector is set at of 220 nm.

Step Six: Buffer Exchange—The remaining organic solvent is removed by buffer exchange, using membrane dialysis. Buffer exchange is carried out in a 50 ml stirred cell with an Amicon YMIO membrane. The ultrafiltration system is prepared according to the depyrogenation protocol before loading the protein solution. The organic solvent is diafiltered by non-pyrogenic distilled water after several runs. hPRL-G129R is retained in the 50 ml retentate solution.

Step Seven: Depyrogenation—Since these products will be used in vivo, a non-pyrogenic product is preferred. Therefore, 100K membrane filtration step is used to remove pyrogens. Depyrogenation is accomplished in a 50 ml stirred cell with a 100K membrane. The stirred cell is treated with 0.1 N NaOH solution according to the depyrogenation protocol. The retentate is washed with non-pyrogenic water three times, and the hPRL-G129R is collected in the permeate. The volume of the permeate is ~100 ml. The concentration of hPRL or hPRL-G129R is determined by a Radio-immuno-matrix Assay (RIMA) assay.

Step eight: Lyophilization—Lyophilization is required for the storage of the final product. hPRL-G129R is more stable in the lyophilized form. All the liquid solvent is removed in a lyophilization equipment with a centrifugal vacuum evaporator. The lyophilized hPRL-G129R sample is then stored in N2 in a −20° C. freezer.

Example 4

Testing the Biological Activities of Purified hPRL and hPRL-G129R via Radioreceptor Binding Assay:

Radioreceptor binding assays are performed as previously described in Chen et al., *Proc. Natl. Acad. Sci USA* 87:5061 (1991), except that PRL is substituted for GH. Briefly, T-47D cells are grown in six-well tissue culture plates until 90% confluent (~$10^5$ cells/well). Monolayers of cells are starved in serum-free RPMI-1640 medium for 2 h. The cells are then incubated at room temperature in serum-free RPMI-1640 containing $8\times10^4$ cpm $^{125}$I hPRL (Specific Activity=30 µCi/µg; NEN Dupont, Boston, Mass.) with or without various concentrations of hPRL (from NIH as standard) and hPRL-G129R. Cells are then washed three times in serum-free RPMI-1640 and solubilized in 0.5 ml of 0.1 N NaOH/1% SDS, and the bound radioactivity is determined by a Gamma counter (ICN Biomedical, model 4/600 plus; Costa Mesa, Calif.). $EC_{50}$ values of hPRL and hPRL-G129R are then determined and expressed as mean±SD. Comparison is made by Student's t-test.

Example 5

Testing the Biological Activities of Purified hPRL and hPRL-G129R via_STAT 5 Phosphorylation/Immunoprecipitation Assay:

T-47D cells are grown in RPMI-1640 medium containing 10% Charcoal Stripped Fetal Bovine Serum (CSFBS; growth medium). For each experiment, cells are passed into 6 well culture plates in growth medium till reach 90% confluence. On the day of the experiment, cells are depleted in serum free media for one hour and incubated in hPRL, hPRL-G129R or combination of two for 30 min. After treatment, T47-D cells are washed once with ice cold PBS and collected by gentle scraping in 1 ml ice cold lysis buffer [20 mM Tris-Cl (pH 7.4), 100 mM NaCl, 2 mM EDTA, 1% NP-40, 1 mM phenylmethylsulfonyl fluoride, 10 ug/ml aprotinin, 10 ug/ml leupeptin]. The lysis mixture is then passed through a 22 gauge needle several times avoiding air bubbles and spin at maximum speed for 20 minutes. The supernatant is then transferred to a new microcentrifuge tube. Five µg of STAT5 monoclonal antibody is then added to 100 microliters (200–500 micrograms total protein) of cell lysate along with 400 microliters of ddH20 and 500 microliters of 2×IP buffer [1% Triton X-100, 150 mM NaCl, 10 mM Tris pH 7.4, 1 mM EDTA, 1 mM EGTA, 0.2 mM sodium vanadate, 0.2 mM PMSF, 0.5% NP-40] to each reaction. After overnight incubation at 4° C. and gentle rotation, 50 microliters of prewashed (1×IP buffer) protein A agarose beads are added to each IP reaction and continue the Incubation for another 2 hours at 4C. At the end of incubation, the agarose beads are washed 3×with 1×IP buffer and the protein are then eluted by resuspending the protein A agarose beads in 50 microliters of 1×SDS PAGE loading buffer. Samples are then subjected to 4–12.5% SDS-PAGE and immune blot analysis using horse radish peroxidase (HRP)-conjugated anti-phosphotyrosine antibody PY20 and ECL reagent kit (Amersham, Ill.). Blots are then exposed to X-ray films and developed using standard procedures (Kodak, Rochester, N.Y.). The results using hPRL and hPRL-G 129R on T-47D human breast cancer cells have demonstrated that hPRL-G129R is able to block the signal transduction induced by hPRL, which suggesting its antagonistic effects.

Example 6

Testing the Biological Activities of Purified hPRL and hPRL-G129R via TUNEL Assay:

This assay (Fluorescein Apoptosis detection system, Promega Corp.) works by labeling the nicks of the fragmented DNA at the 3-OH ends. The fluorescein labeled dUTP is incorporated at the 3-OH ends by terminal deoxynucleotidyl transferase. T47-D human breast cancer cells are used. Before the assay, the breast cancer cells are switched to 10% Charcoal-striped Fetal Bovine Serum (CCS) for a week. Subsequently, the cells are plated onto an 8 chambered slide system (Lab TekII) at a confluence of 60–70% per chamber. The next day the breast cancer cells are treated with various concentrations of hPRL-G129R in conditioned medium (0.5% CSS). After about 24 to 48 hours, the chambers are dismantled and the assay is performed as per the manufacturer's instructions. The slides are examined under a FITC filter using an Olympus IX 70 microscope system.

Example 7

Determination of the Concentration of the hPRLA-IL-2 Fusion Protein:

SDS-PAGE and immune blotting analysis is performed SDS-PAGE and immune blotting analysis is performed to further ensure that the expressed hPRLA-IL-2 fusion protein possesses the appropriate molecular mass. The culture fluid from transiently transfected mouse L cells is collected and subjected to 15% SDS-PAGE that is performed routinely in our laboratory using a Bio-Rad Protean II or Mini-Protean II system (Bio-Rad, Hercules, Calif.). Following protein transfer, the nitrocellulose paper is blocked with 2% gelatin in TBS with gentle agitation for 1 hour at room temperature, and then washed three times with 0.05% Tween 20 in TBS (5 min per wash). Polyclonal rabbit anti-hPRL (from BioDesign International, Kennebunk, Me., 1:200 dilution) in 1% gelatin/TBS is added to the nitrocellulose membrane and incubated overnight at room temperature with gentle agitation. After removing the primary antibody, the nitrocellulose paper is washed three times with 0.05% Tween 20 in TBS and subsequently incubated for 2 hours at room temperature in the presence of a goat anti-rabbit IgG horseradish peroxidase (HRP) conjugate (Boehringer Mannheim Biochemicals) in 1% Gelatin/TBS. Following incubation with secondary antibody, the nitrocellulose is washed three times with 0.05% Tween 20 in TBS.

To visualize the protein bands, the nitrocellulose paper is incubated for 10 min in a mixture of 50 ml of 0.018% $H_2O_2$ (v/v) in TBS and 10 ml of methanol containing 30 mg of HRP color development reagent (Bio Rad). The nitrocellulose paper is rinsed with water, air-dried and photographed. Purified hPRL, and IL-2 (Accurate Chemical & Scientific Corp. Westbury, N.Y.) is used to quantify the expressed hPRLA-IL-2 level by photographic and densitometric methods (Fernadez and Kopchick, 1990).

Example 8

Determining the Binding Features of hPRLA-IL2 Fusion Protein Using a Radioreceptor Binding Assay and Human Breast Cancer Cells:

The main purpose of this experiment is to compare the binding affinity of hPRL, hPRLA and the hPRLA-IL-2 fusion protein using human breast cancer cells to confirm that the fusion of hPRLA to IL-2 does not affect its binding ability to hPRLR in breast cancer cells.

Radioreceptor binding assays are performed as described in Chen et al., *Proc. Natl. Acad. Sci. USA* 87:5061 (1991). Briefly, T-47D cells were grown in six-well tissue culture plates until 90% confluent ($^\sim10^5$ cells/well). Monolayers of cells were starved in serum-free RPMI-1640 medium for 2 h. The cells were then incubated at room temperature in serum-free RPMI-1640 containing $8\times10^4$ cpm $^{125}$I hPRL (Specific Activity=30 µCi/µg; NEN Dupont, Boston, Mass.) with or without various concentrations of hPRL (from NIH as standard) and hPRL-G129R. Cells were then washed three times in serum-free RPMI-1640 and solubilized in 0.5 ml of 0.1 N NaOH/1% SDS, and the bound radioactivity was determined by a Gamma counter (ICN Biomedical, model 4/600 plus; Costa Mesa, Calif.). $EC_{50}$ values of hPRL and hPRL-G129R were then determined and expressed as mean±SD. Comparison was made by Student's t-test. Nonspecific binding is determined by adding 1 µg/ml of unlabeled hPRL+1 µg of IL-2.

Example 9

Comparison of Biological Activities of IL-2, hPRLA and hPRLA-IL-2 Fusion Protein using Cell Proliferation Assays:

Two types of cell proliferation assays are used in this study to make sure that hPRLA-IL2 fusion protein retains IL-2 like activity as well as hPRLA-like activity. Murine T cell line (HT-2 cells) is a IL-2-responsive cell line, which typically has been used to examine the biological activities of recombinant mouse and human IL-2, is used to test the IL-2-like activity of the fusion protein (Taniguchi et al., 1983; Rosenberg et al., 1984). In addition, the fusion protein is tested for its potential antagonistic activity using human breast cancer cells.

A human breast cancer cell line (T47-D) is used (from ATCC). The cells are grown in corresponding culture media according to ATCC recommendations. The assay conditions are described by Ginsburg and Vonderharr (1995) and may be modified according to each cell line. In general, cells are maintained at 37° C. in a humidified atmosphere of 5% $CO_2$ in air. For individual growth experiments, cells are plated in 12-well culture plates at a density of approximately $2\times10^4$ ml/well. Cells are allowed to attach for one day and the media are removed and changed to serum-free conditions with media containing ITS+(insulin-transferrin-selenium-BSA-linoleic acid culture supplement; Collaborative Research Bedford, Mass.). Various concentrations of hPRL, hPRLA, hPRLA-IL-2 or in combination of two (hPRLA: hPRL or hPRLA-IL-2:hPRL at 1:1, 5:1, 10:1 etc.) are added. After an additional three days in culture, cells are harvested after brief trypsinization and counted in a cell counter.

Example 10

In vivo Studies Using Syngeneic Mouse Models to Test the Anti-Tumor Activities of hPRLA-IL-2 Fusion Protein:

The ultimate test of the anti-tumor effects of the hPRLA-IL-2 is the in vivo test. For this purpose, syngeneic immune competent C3H mice and breast tumor cells derived from the same strain of mice to test the potential anti-tumor activities of the fusion protein are used.

In particular, CRL-6326 and/or CRL-6378 mouse mammary gland cancer cells are used. To ascertain the status of the PRLR on those cells, a radioreceptor binding assay is performed on these cells to ensure that they contain PRLR. Two cell lines are used as positive and negative controls. One cell line is C3H-derived mouse L cells purchased from ATCC. These transformed fibroblasts induce tumors if injected subcutaneously. Since GHR or PRLR are non-detectable on the L cell surface (data not shown), the L cells are used as non breast cancer controls. A mouse L cell line that is stably transfected with hPRLR cDNA is also used to induce tumor in C3H mice. The tumor induced by these cells is considered as a positive control due to the high levels of hPRLR on the cell surface.

Subcutaneous tumors is induced by inoculation of $5\times10^6$ cancer cells to serve as a cancer model. It induces tumors to grow to a volume of 25 µl within 10 days Reisfeld et al. (1996), supra. At that point, animals are treated by iv. administration of IL-2, PRLA, and PRLA-IL-2 fusion protein for 7 days. Two doses (5µg and 25 µg per injection) for each group are used. At the end of the treatment, the animals are sacrificed and the tumor weight between animals receiving either no treatment or treatment with IL-2, hPRLA or hPRLA-IL-2 fusion proteins are measured and the statistical analysis is applied.

Tumor immunohistological evaluation is also carried out to examine the evidence of cellular infiltration in situ. Briefly, frozen sections are fixed in cold acetone for 10 min followed by removal of endogenous peroxidase with 0.03% $H_2O_2$ and blocking of collagenous elements with 10% serum in 1% BSA/PBS. The CD45 specific antibody is then overlayed onto serial sections at predetermined dilutions (~20 μg/ml) and the slides are incubated in a humid chamber for 30 min. With PBS washes between every step, a biotinylated secondary antibody is applied for 10 min followed by alkaline phosphatase linked to streptavidin for 10 min. After another wash, the substrate is added and the slides are incubated in the dark for 20 min. After a wash in PBS, the slides are counter stained, mounted, and viewed using Olympus (New Hyde Park, N.Y.) BH2 microscope.

The following table shows the experimental design of using syngeneic mice and tumor cells to test the biological activities of hPRLA-IL2 fusion protein.

| Group/Tumor cell Injection | C3H Mouse Mouse L cells | C3H Mouse HpRLR+/ Mouse L cells | C3H Mouse Mouse Breast Cancer Cells |
|---|---|---|---|
| Treatment A | Control | Control | Control |
| Treatment B (5 μg, 25 μg) | IL-2 | IL-2 | IL-2 |
| Treatment C (5 μg, 25 μg) | HPRLA | HPRLA | hPRLA |
| Treatment D (5 μg, 25 μg) | hPRLA-IL2 | HPRLA-IL2 | hPRLA-IL2 |

What is claimed is:

1. A method for treating prostate and breast cancer, comprising administering to a patient that has prostate or breast cancer a protein that comprises a receptor-antagonizing domain and a positive immunomodulator domain, wherein the receptor-antagonizing domain comprises SEQ ID NO: 35 but has an amino acid substitution at position 129, and the positive immunomodulator domain is a cytokine selected from the group consisting of IL-2, IL-12, and IFNγ.

2. The method according to claim 1, wherein the cytokine is IL-2.

3. The method according to claim 1, wherein the cytokine is IL-12.

4. The method according to claim 1, wherein the cytokine is IFNγ.

5. The method according to claim 1, wherein cells of the cancer overexpress a prolactin receptor at levels greater than in normal, healthy cells.

6. A method for inducing an immune response in an individual that has cancerous prostate or breast cells, comprising administering to said individual a protein comprising (i) a prolactin-antagonist domain comprising SEQ ID NO: 35 but has an amino acid substitution at position 129, and (ii) an immunomodulatory domain, wherein said immunomodulatory domain is a cytokine selected from the group consisting of IL-2, IL-12, and INFγ.

7. The method of claim 6, wherein said prolactin-antagonist domain comprises a protein consisting essentially of the amino acid sequence of SEQ ID NO. 34.

8. The method of claim 6, wherein the amino acid at position 129 is arginine.

9. The method of claim 6, wherein said cancerous cells express prolactin receptors at a level greater than that of normal, healthy cells.

10. The method of claim 6, wherein said cytokine is IL-2.

11. The method of claim 6, wherein said cytokine is IL-12.

12. The method of claim 6, wherein said cytokine is IFNγ.

13. A method for inducing an immune response in an individual that has cancerous prostate or breast cells, comprising administering to said individual a protein comprising (i) a domain that binds to a receptor expressed on a cancer cell altering the function of said receptor, and (ii) another domain that elicits an immune response that is targeted to said cancer cell, wherein the domain that binds to a receptor expressed on a cancer cell is a prolactin antagonist domain comprising SEQ ID NO: 35 but has an amino acid substitution at position 129, and the domain that elicits an immune response is a cytokine selected from the group consisting of IL-2, IL-12, and IFNγ.

14. The method of claim 13, wherein the prolactin-antagonist domain has an arginine at position 129.

15. The method of claim 14, wherein the prolactin-antagonist domain comprises SEQ ID NO. 34.

16. The method of claim 1, wherein the receptor antagonizing domain comprises SEQ ID NO: 34.

17. The method of claim 1, wherein the amino acid at position 129 is a bulky side-chain amino acid.

18. The method of claim 6, wherein the amino acid at position 129 is a bulky side-chain amino acid.

19. The method of claim 7, wherein said cancerous cells express prolactin receptors at a level greater than that of normal, healthy cells.

20. The method of claim 7, wherein said cytokine is IL-2.

21. The method of claim 7, wherein said cytokine is IL-12.

22. The method of claim 7, wherein said cytokine is IFNγ.

* * * * *